(12) United States Patent
Govari

(10) Patent No.: US 9,226,710 B2
(45) Date of Patent: Jan. 5, 2016

(54) WIRELESS CATHETER WITH BASE WIRELESS TRANSCEIVER

(75) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 354 days.

(21) Appl. No.: 13/531,828

(22) Filed: Jun. 25, 2012

(65) Prior Publication Data

US 2013/0345549 A1  Dec. 26, 2013

(51) Int. Cl.
*A61B 5/05* (2006.01)
*A61B 5/06* (2006.01)
*A61B 5/00* (2006.01)
*H01Q 7/00* (2006.01)

(52) U.S. Cl.
CPC ............... *A61B 5/6852* (2013.01); *A61B 5/065* (2013.01); *A61B 5/6885* (2013.01); *H01Q 7/00* (2013.01)

(58) Field of Classification Search
USPC ........ 606/1–3, 41, 32, 439, 27; 600/372–390, 600/414, 423–424; 601/1–3, 41
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,558,091 A | 9/1996 | Acker et al. | |
| 5,983,126 A | 11/1999 | Wittkampf | |
| 6,172,499 B1 | 1/2001 | Ashe | |
| 6,177,792 B1 | 1/2001 | Govari et al. | |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,788,967 B2 | 9/2004 | Ben-Haim et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2006/0241441 A1* | 10/2006 | Chinn | 600/439 |
| 2007/0083193 A1* | 4/2007 | Werneth et al. | 606/41 |
| 2007/0100332 A1 | 5/2007 | Paul et al. | |
| 2007/0161904 A1 | 7/2007 | Urbano | |
| 2009/0093806 A1 | 4/2009 | Govari et al. | |
| 2009/0138007 A1 | 5/2009 | Govari et al. | |
| 2010/0145281 A1 | 6/2010 | Denault et al. | |
| 2010/0238278 A1* | 9/2010 | Rovegno | 348/75 |
| 2010/0298895 A1 | 11/2010 | Ghaffari et al. | |

FOREIGN PATENT DOCUMENTS

WO    WO 96/05768 A1    2/1996

* cited by examiner

*Primary Examiner* — Long V Le
*Assistant Examiner* — Lawrence Laryea
(74) *Attorney, Agent, or Firm* — Wayne C. Jaeschke, Jr.

(57) ABSTRACT

A medical probe, including a flexible insertion tube having a distal end for insertion into a body cavity and including one or more sensors mounted in the distal end, and a handle coupled to a proximal end of the insertion tube. The medical probe also includes a cable having a proximal end and a distal end, which is coupled to the handle so as to receive signals conveyed through the insertion tube from the one or more sensors, and a base unit coupled to the proximal end of the cable. The base unit contains a power source, and a probe wireless transceiver coupled to receive the signals from the cable and to communicate over a wireless connection with a control console.

14 Claims, 3 Drawing Sheets

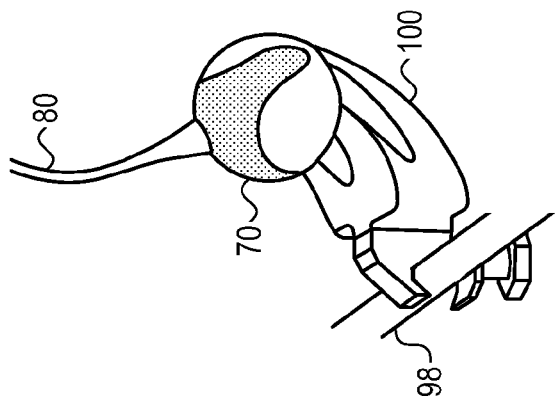
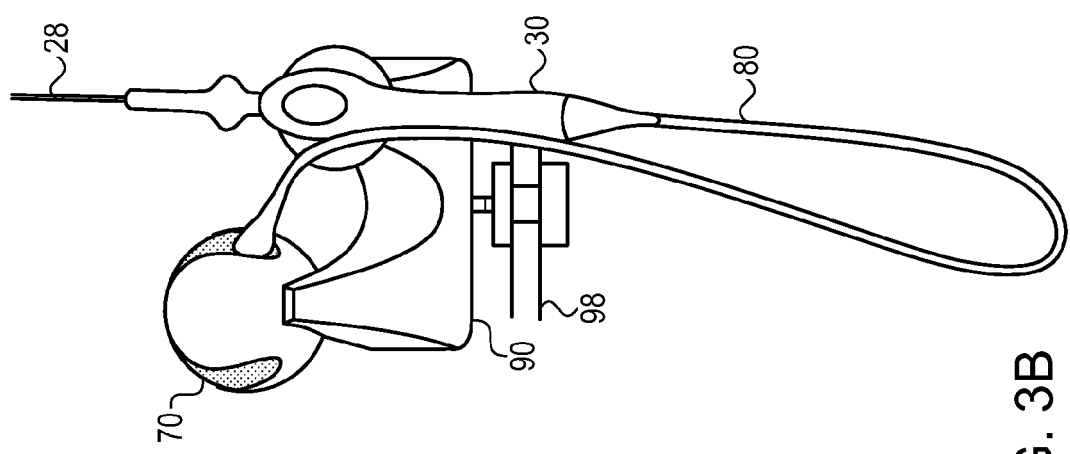
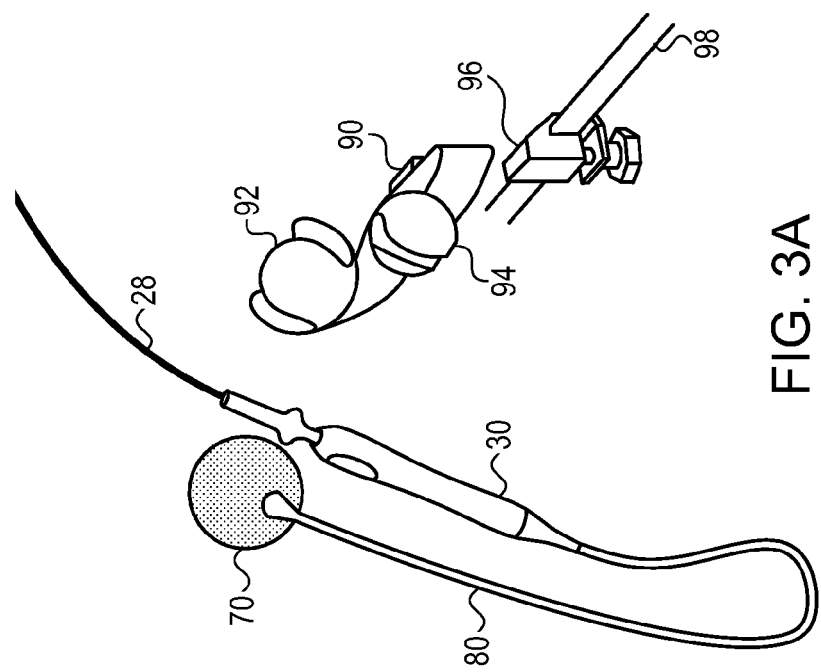

WIRELESS CATHETER WITH BASE WIRELESS TRANSCEIVER

FIELD OF THE INVENTION

The present invention relates generally to invasive probes, and specifically to producing an invasive probe fitted with a wireless transceiver.

BACKGROUND OF THE INVENTION

A wide range of medical procedures involve placing objects, such as sensors, tubes, catheters, dispensing devices and implants, within a patient's body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332, 2009/0093806 and 2009/0138007, whose disclosures are incorporated herein by reference, describe methods of sensing contact pressure between the distal tip of a catheter and tissue in a body cavity using a force sensor embedded in the catheter.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

There is provided, in accordance with an embodiment of the present invention a medical probe, including a flexible insertion tube having a distal end for insertion into a body cavity and including one or more sensors mounted in the distal end, a handle coupled to a proximal end of the insertion tube, a cable having a proximal end and a distal end, which is coupled to the handle so as to receive signals conveyed through the insertion tube from the one or more sensors. The probe includes a base unit coupled to the proximal end of the cable, and containing a power source, and a probe wireless transceiver coupled to receive the signals from the cable and to communicate over a wireless connection with a control console.

In some embodiments, the power source may be selected from a list including a battery, a power outlet and a wireless energy transfer system. In additional embodiments, the medical probe may include a spherical orb configured to house the base unit, and a socket configured to retain and allow a rotation of the spherical orb. In alternative embodiments, the medical probe may include a catheter holder configured to grasp the handle. In further embodiments, each of the one or more sensors may be selected from a list consisting of an electrode, a force sensor and a position sensor. In additional embodiments, the control console may include a console wireless transceiver and a processor configured to receive, via the wireless connection, measurement signals from the one or more sensors. In some embodiments, the medical probe may have no physical connection to the console. In additional embodiments, the medical probe may include one or more electrodes mounted on the distal end and coupled to the power source, and the probe wireless transceiver is configured to receive, via the wireless connection, an ablation signal from the processor, and the one or more electrodes are configured to perform an ablation on a wall of the body cavity responsively to the ablation signal.

There is also provided, in accordance with an embodiment of the present invention, a method, including inserting, using a handle coupled to a proximal end of a flexible insertion tube of a medical probe, a distal end of the flexible insertion tube into a body cavity, receiving, by a cable having a proximal end and a distal end which is coupled to the handle, signals, conveyed through the insertion tube, from one or more sensors mounted in the distal end of the insertion tube, and coupling a base unit to the proximal end of the cable, the base unit containing a power source, and a probe wireless transceiver coupled to receive the signals from the cable and to communicate over a wireless connection with a control console.

BRIEF DESCRIPTION OF THE DRAWINGS

The disclosure is herein described, by way of example only, with reference to the accompanying drawings, wherein:

FIGS. 3A and 3B are schematic pictorial illustrations of a fixture configured to hold a base unit and a handle of the probe, in accordance with a first embodiment of the present invention; and FIG. 3C is a schematic pictorial illustration of the fixture configured to hold the base unit, in accordance with a second embodiment of the present invention.

DETAILED DESCRIPTION OF EMBODIMENTS

Overview

Various diagnostic and therapeutic procedures, such as cardiac ablation and intracardiac electrical mapping, use an invasive probe, such as a catheter, whose distal tip is fitted with at least one electrode. The electrode is typically operated when the probe is pressed against a wall (also referred to herein as tissue) of a body cavity. In these procedures, it is usually important to ascertain both the precise location of the probe in the body cavity, and the force that the distal tip is exerting on the body cavity wall. Therefore, some catheters comprise position sensors for ascertaining the location of the distal tip and force sensors for measuring the force exerted by the probe on intra-body tissue, such as the endocardium.

Embodiments of the present invention form a "wireless catheter" by incorporating a wireless transceiver into the catheter, thereby reducing (and possibly eliminating) the number of physical links between the patient and a console. Since space limitations may preclude mounting the wireless transceiver and a power source in the catheter's handle, a base unit containing a transceiver-battery combination can be coupled to a proximal end of the handle by a cable.

In some embodiments, a fixture can be configured to hold a housing for the base unit and/or the handle. The fixture may include a holder where the operator can "park" the handle when the catheter is not being used. Additionally, the base unit housing can be configured as a spherical orb, and the fixture may include a socket configured to retain and allow a rotation of the spherical orb. The socket-orb configuration can function as a ball joint, within which the base unit is able to swivel, so that when the catheter holder is removed from the mount and manipulated, the cable does not restrict the motion of the handle.

Incorporating a wireless transceiver into a catheter system can help reduce clutter resulting from physical connections between the catheter and the console, thereby enhancing safety during a medical procedure. By eliminating the need for cabling between the catheter and the console, embodiments of the present invention can make it simple to add additional wireless catheters into an on-going procedure, rather than adding catheters requiring a physical connection to the console.

System Description

Figure 1:
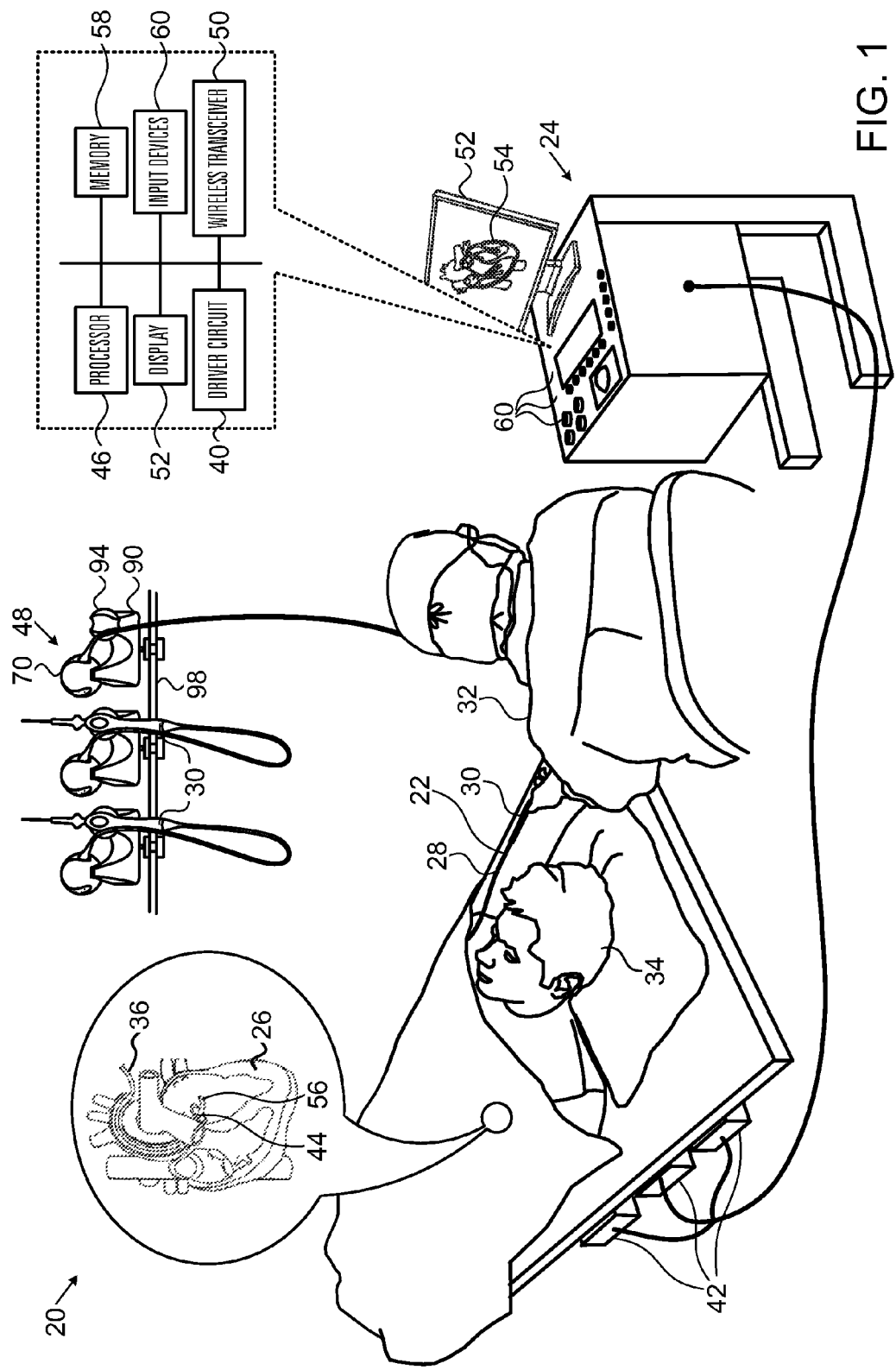
FIG. 1 is a schematic pictorial illustration of a medical system that implements wireless communication, in accordance with an embodiment of the present invention.

FIG. 1 is a schematic pictorial illustration of a medical system 20 that implements wireless communication, in accordance with an embodiment of the present invention. System 20 may be based, for example, on the CARTO™ system, produced by Biosense Webster Inc. (Diamond Bar, Calif.). System 20 comprises a probe 22, such as a catheter, and a control console 24. In the embodiment described hereinbelow, it is assumed that probe 22 is used for diagnostic or therapeutic treatment, such as for mapping electrical potentials in a heart 26 or performing ablation of heart tissue. Alternatively, probe 22 may be used, mutatis mutandis, for other therapeutic and/or diagnostic purposes in the heart or in other body organs.

Probe 22 comprises a flexible insertion tube 28, and a handle 30 coupled to the proximal end of the insertion tube. When probe 22 is not being used, handle 30 can be stored in a probe holder 94 of a fixture 90, which may typically be affixed to a mounting bar 98. The configuration of fixture 90 and mounting bar 98 are described in detail hereinbelow. By removing then manipulating handle 30, operator 32 can insert probe 22 through the vascular system of a patient 34 so that a distal end 36 of probe 22 enters a chamber of heart 26.

In the configuration shown in FIG. 1, multiple probes, each generally similar to probe 22, can be stored in a corresponding multiple of fixtures, each generally similar to fixture 90, affixed to mounting bar 98. During a medical procedure, an operator 32, such as a cardiologist, can select a given probe by removing its handle from its probe holder.

System 20 typically uses magnetic position sensing to determine position coordinates of distal end 36 inside heart 26. Console 24 comprises a driver circuit 40 which drives field generators 42 to generate magnetic fields within the body of patient 34. Typically, field generators 42 comprise coils, which are placed below the patient's torso at known positions external to patient 34. These coils generate magnetic fields in a predefined working volume that contains heart 26. A magnetic field sensor 44 within distal end 36 of probe 22 (sensor 44 is shown in more detail in FIG. 2) generates electrical signals in response to the magnetic fields from the coils, thereby enabling console 24 to determine the position of distal end 36 within the chamber.

Although in the present example system 20 measures the position of distal end 36 using magnetic-based sensors, other position tracking techniques may be used (e.g., impedance-based sensors). Magnetic position tracking techniques are described, for example, in U.S. Pat. Nos. 5,391,199 and 6,690,963 referenced above, and in in U.S. Pat. Nos. 5,443,489, 6,788,967, 5,558,091, 6,172,499 and 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

A signal processor 46 processes these signals in order to determine the position coordinates of distal end 36, typically including both location and orientation coordinates. The method of position sensing described hereinabove is implemented in the above-mentioned CARTO™ system and is described in detail in the patents and patent applications cited above.

Signal processor 46 typically comprises a general-purpose computer, with suitable front end and interface circuits for receiving signals from probe 22 and controlling the other components of console 24. Processor 46 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 46 may be carried out by dedicated or programmable digital hardware components.

A probe wireless transceiver 48 coupled to probe 22 is configured to communicate with processor 40 over a wireless connection via a console wireless transceiver 50. For example, wireless transceivers 48 and 50 may comprise Bluetooth or Wireless Universal Serial Bus (USB) transceivers. Based on the signals received from probe 22 (via wireless transceiver 50) and other components of system 20, processor 46 drives a display 52 to present operator 32 with an image 54 showing the position of distal end 36 in the patient's body, as well as status information and guidance regarding the procedure that is in progress.

In the present embodiment, processor 46 monitors measurements received from position sensor 44 and a force sensor 56 within distal end 36 (force sensor 56 is shown in more detail in FIG. 2), typically during periods in which the catheter is believed to be pressing against endocardial tissue of heart 26. Processor 46 stores data representing image 54 in a memory 58. In some embodiments, operator 32 can manipulate image 54 using one or more input devices 60.

Alternatively or additionally, system 20 may comprise an automated mechanism (not shown) for maneuvering and operating probe 22 within the body of patient 34. Such mechanisms are typically capable of controlling both the longitudinal motion (advance/retract) of probe 22 and transverse motion (deflection) of distal end 36 of the probe. In such embodiments, processor 46 generates a control input for controlling the motion of probe 22 based on the signals provided by the magnetic field sensor in the probe.

Although FIG. 1 shows a particular system configuration, other system configurations can also be employed to implement embodiments of the present invention, and are thus considered to be within the spirit and scope of this invention. For example, the methods described hereinbelow may be applied using position sensors of types other than the magnetic field sensor described above, such as impedance-based or ultrasonic position sensors. The term "position transducer"

as used herein refers to an element mounted on probe 22 which causes console 24 to receive signals indicative of the coordinates of the element. The position sensor may thus comprise a receiver on the probe, which generates a position signal to the control unit based on energy received by the sensor; or it may comprise a transmitter, emitting energy that is sensed by a receiver external to the probe. Furthermore, the methods described hereinbelow may similarly be applied in therapeutic and diagnostic applications using not only catheters, but also probes of other types, both in the heart and in other body organs and regions.

Other elements of system 20 illustrated in FIG. 1, such as a base unit 70, are described in more detail below.

Figure 2:
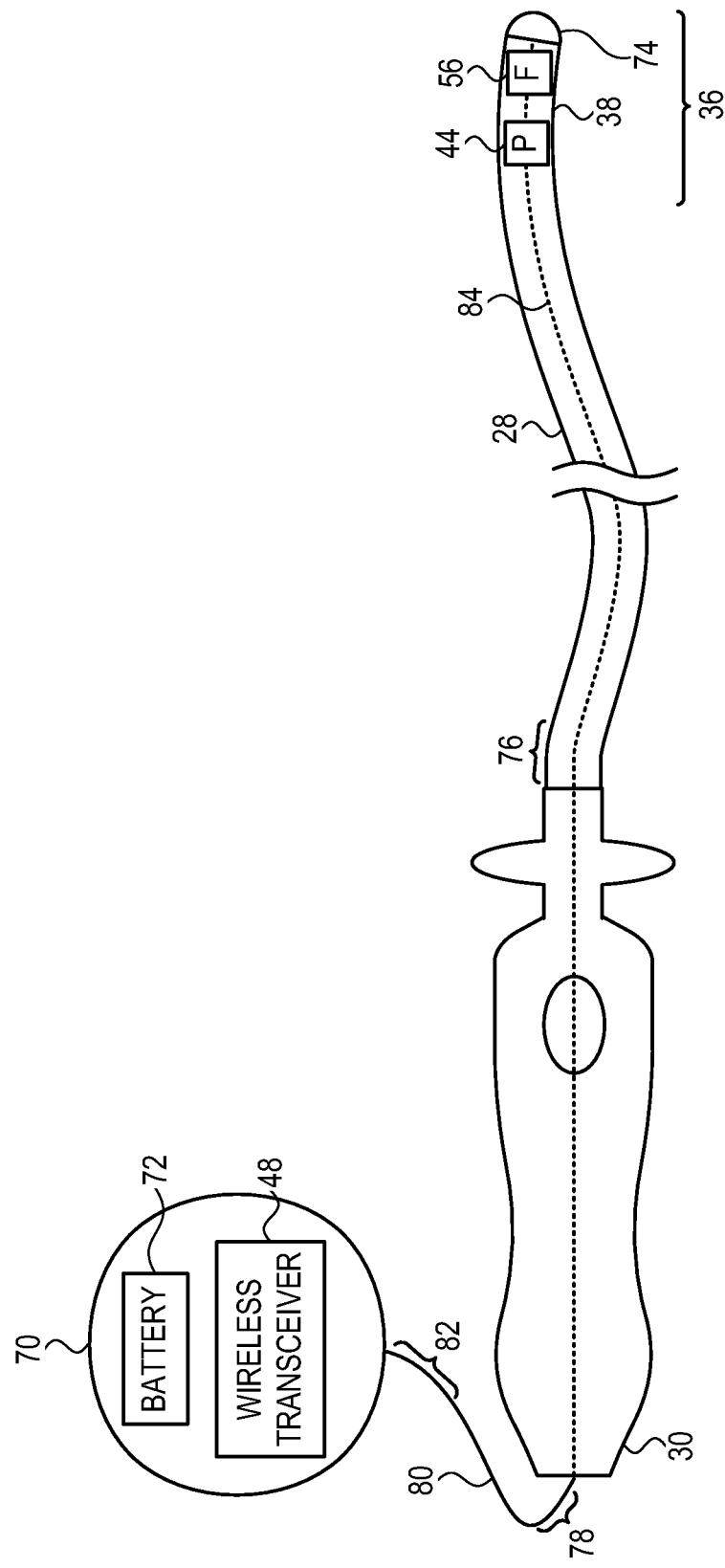
FIG. 2 is a schematic sectional view of a probe configured to communicate with a control console over a wireless connection, in accordance with an embodiment of the present invention.

FIG. 2 is a schematic sectional view of probe 22, in accordance with an embodiment of the present invention. Specifically, FIG. 2 shows functional elements of probe 22 and base unit 70 coupled to the probe. Base unit 70 comprises wireless transceiver 48 and a battery 72. While the example in FIG. 2 shows battery 72 as a power source, other power sources are considered to be within the spirit and scope of the present invention. For example, the power source may comprise a wired connection to either a battery external to the base unit or a standard alternating current (AC) power outlet. Alternatively, power can be conveyed to the probe via a wireless energy transfer system.

An ablation electrode 74 at a distal tip 38 of the probe is typically made of a metallic material, such as a platinum/iridium alloy or another suitable material. Alternatively, multiple electrodes (not shown) may be positioned along the length of the probe.

Position sensor 44 transmits a signal to console 24 that is indicative of the location coordinates of distal end 36. Position sensor 44 may comprise one or more miniature coils, and typically comprises multiple coils oriented along different axes. Alternatively, position sensor 44 may comprise either another type of magnetic sensor, an electrode which serves as a position sensor, or position sensors of other types, such as impedance-based or ultrasonic position sensors. Although FIG. 2 shows a probe with a single position sensor, embodiments of the present invention may utilize probes with more than one position sensor.

In an alternative embodiment, the roles of position sensor 44 and magnetic field generators 42 may be reversed. In other words, driver circuit 40 may drive a magnetic field generator in distal end 36 to generate one or more magnetic fields. The coils in generator 42 may be configured to sense the fields and generate signals indicative of the amplitudes of the components of these magnetic fields. Processor 46 receives and processes these signals in order to determine the position coordinates of distal end 36 within heart 26.

Force sensor 56 measures a force applied by distal tip 38 to the endocardial tissue of heart 26 by conveying a signal to the console that is indicative of the force exerted by the distal tip on the intra-body tissue. In one embodiment, the force sensor may comprise a magnetic field transmitter and receiver connected by a spring in distal end 36, and may generate an indication of the force based on measuring the deflection of the spring. Further details of this sort of probe and force sensor are described in U.S. Patent Application Publications 2009/0093806 and 2009/0138007 referenced above. Alternatively, distal end 36 may comprise another type of force sensor.

Handle 30 is configured to be grasped by operator 32, and is coupled to a proximal end 76 of insertion tube 28 and a distal end 78 of a cable 80. A proximal end 82 of cable 80 is coupled to base unit 70. The distal end of cable 80 is coupled to position sensor 44, force sensor 56 and electrode 74 via a connection 84 that is contained within insertion tube 28 and handle 30. While (for illustrative purposes) FIG. 2 shows a single connection 84 coupling the electrode and the sensors to cable 80, there are typically multiple connections contained within the insertion tube and the handle. Connection 84 typically comprises a metallic conductor and/or an optical fiber.

In operation, cable 80 receives signals from the position sensor, the force sensor and the electrode (when measuring electrical potentials values in the heart) that are conveyed through insertion tube 28 (i.e., via connection 84). Wireless transceiver 48 receives the signals from cable 80, and communicates the signals to console 24 over a wireless connection.

In some embodiments wireless transceiver 48 can be configured to receive wireless signals to control an ablation performed by electrode 74. During an ablation procedure, processor 46 conveys, via the wireless connection, an ablation signal to probe 22. Upon wireless transceiver 48 receiving the ablation signal, the probe performs the ablation by conveying an electrical current to electrode 74.

FIGS. 3A and 3B are schematic pictorial illustrations of fixture 90 that is configured to hold base unit 70 and handle 30, in accordance with a first embodiment of the current invention. In the configuration shown in FIGS. 3A and 3B, base unit 70 is configured as a spherical orb that houses wireless transmitter 48 and battery 72, and fixture 90 comprises a socket 92, probe holder 94 and a clamp 96. Clamp 96 can be used to affix fixture 90 to mounting bar 98 that is typically within reach of the operator. As shown in FIG. 1, multiple wireless probes can be made accessible to operator 32 by affixing multiple fixtures to mounting bar 98.

Probe holder 94 is configured to grasp handle 30 when probe is not being used. Socket 92 is configured to retain spherical base unit 70, and allow a rotation of the spherical base unit within the socket, so that the sphere rotating in the socket acts in a manner similar to a ball joint. In other words, when operator 32 removes handle 30 from holder 94 and manipulates the probe, the ball joint configuration of the sphere and the socket does not restrict the motion of the handle.

FIG. 3C is a schematic pictorial illustration of a fixture 100 configured to hold base unit 70, in accordance with a second embodiment of the present invention. In contrast to fixture 90, fixture 100 holds only base unit 70. In the configuration shown in FIG. 3C, a separate catheter holding fixture (not shown) can be used to grasp handle 30.

Because of power capacity limitations of battery 72, the wireless catheter may not be capable of relatively high power/high energy operation, such as is needed for an ablation procedure. In some embodiments, as described supra, electrical current can be conveyed from an external power source to probe 22 via a wired connection or a wireless energy transfer system that is incorporated into fixture 90 or 100, and/or the mounting bar, thereby eliminating restrictions caused by the current being supplied by battery 72.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical probe, comprising:
   a flexible insertion tube having a distal end for insertion into a body cavity and comprising one or more sensors mounted in the distal end;
   a handle coupled to a proximal end of the insertion tube;
   a cable having a proximal end and a distal end, which is coupled to the handle so as to receive signals conveyed through the insertion tube from the one or more magnetic field sensors; and
   a base unit coupled to the proximal end of the cable, and containing:
   a power source;
   a probe wireless transceiver coupled to receive the signals from the cable and to communicate over a wireless connection with a control console; and
   a spherical orb configured to house the base unit, and a socket configured to retain and allow a rotation of the spherical orb, wherein the power source is selected from a list comprising a battery, a power outlet and a wireless energy transfer system.

2. The medical probe according to claim 1, and comprising a catheter holder configured to grasp the handle.

3. The medical probe according to claim 1, wherein each of the one or more sensors is selected from a list consisting of an electrode, a force sensor and a position sensor.

4. The medical probe according to claim 1, wherein the control console comprises a console wireless transceiver and a processor configured to receive, via the wireless connection, measurement signals from the one or more sensors.

5. The medical probe according to claim 1, wherein the medical probe has no physical connection to the console.

6. The medical probe according to claim 1, and comprising one or more electrodes mounted on the distal end and coupled to the power source.

7. The medical probe according to claim 6, wherein the probe wireless transceiver is configured to receive, via the wireless connection, an ablation signal from the processor, and the one or more electrodes are configured to perform an ablation on a wall of the body cavity responsively to the ablation signal.

8. A method, including:
   inserting, using a handle coupled to a proximal end of a flexible insertion tube of a medical probe, a distal end of the flexible insertion tube into a body cavity;
   receiving, by a cable having a proximal end and a distal end which is coupled to the handle, signals, conveyed through the insertion tube, from one or more magnetic field sensors mounted in the distal end of the insertion tube;
   coupling a base unit to the proximal end of the cable, the base unit containing:
   a power source, and
   a probe wireless transceiver coupled to receive the signals from the cable and to communicate over a wireless connection with a control console, wherein the power source is selected from a list comprising a battery, a power outlet and a wireless energy transfer system; and
   configuring the base unit as a spherical orb, and retaining the spherical orb in a socket configured to allow a rotation of the spherical orb.

9. The method according to claim 8, and comprising storing the probe in a catheter holder configured to grasp the handle.

10. The method according to claim 8, wherein each of the one or more sensors is selected from a list consisting of an electrode, a force sensor and a position sensor.

11. The method according to claim 8, and comprising receiving, by the control console via the wireless connection, measurement signals from the one or more sensors.

12. The method according to claim 8, wherein the medical probe has no physical connection to the console.

13. The method according to claim 8, and comprising mounting one or more electrodes on the distal end, and coupling the one or more electrodes to the power source.

14. The method according to claim 13, and comprising receiving, by the probe via the wireless connection, an ablation signal from the console, and performing, by the one or more electrodes, an ablation on a wall of the body cavity responsively to the ablation signal.

* * * * *